(12) United States Patent
Birkbeck

(10) Patent No.: US 9,156,770 B2
(45) Date of Patent: Oct. 13, 2015

(54) PROCESS FOR THE PREPARATION OF BETA-SANTALOL

(75) Inventor: Anthony A. Birkbeck, Geneva (CH)

(73) Assignee: Firmenich SA, Geneva (CH)

( * ) Notice: Subject to any disclaimer, the term of this patent is extended or adjusted under 35 U.S.C. 154(b) by 84 days.

(21) Appl. No.: 14/125,876

(22) PCT Filed: Jun. 28, 2012

(86) PCT No.: PCT/EP2012/062615
§ 371 (c)(1),
(2), (4) Date: Dec. 12, 2013

(87) PCT Pub. No.: WO2013/001027
PCT Pub. Date: Jan. 3, 2013

(65) Prior Publication Data
US 2014/0187811 A1    Jul. 3, 2014

Related U.S. Application Data

(60) Provisional application No. 61/503,244, filed on Jun. 30, 2011.

(30) Foreign Application Priority Data

Jun. 30, 2011 (EP) .................................. 11172038

(51) Int. Cl.
| | |
|---|---|
| C07C 67/293 | (2006.01) |
| C07C 67/297 | (2006.01) |
| C07C 67/00 | (2006.01) |
| C07C 67/283 | (2006.01) |
| C07C 69/16 | (2006.01) |
| C07C 69/28 | (2006.01) |
| C07C 69/63 | (2006.01) |
| C07C 29/128 | (2006.01) |
| C07C 47/21 | (2006.01) |
| C07C 69/145 | (2006.01) |
| C07C 69/602 | (2006.01) |

(52) U.S. Cl.
CPC ........... *C07C 67/293* (2013.01); *C07C 29/1285* (2013.01); *C07C 47/21* (2013.01); *C07C 67/00* (2013.01); *C07C 67/283* (2013.01); *C07C 67/297* (2013.01); *C07C 69/145* (2013.01); *C07C 69/16* (2013.01); *C07C 69/28* (2013.01); *C07C 69/602* (2013.01); *C07C 69/63* (2013.01); *C07C 2102/42* (2013.01)

(58) Field of Classification Search
None
See application file for complete search history.

(56) References Cited

U.S. PATENT DOCUMENTS

| | | | |
|---|---|---|---|
| 3,662,008 A | 5/1972 | Kretschmar et al. | |
| 3,679,756 A | 7/1972 | Kretschmar et al. | |

FOREIGN PATENT DOCUMENTS

| | | | |
|---|---|---|---|
| EP | 10213 | | 4/1980 |
| EP | 2119714 A1 | | 11/2009 |
| WO | WO 2006120639 A2 | | 11/2006 |
| WO | WO 2008120175 A1 | | 10/2008 |
| WO | 2009141781 | * | 11/2009 |
| WO | WO 2009141781 A1 | | 11/2009 |

OTHER PUBLICATIONS

Fehr et al., Chem. Eur. Journal., 2010, 17, 1257-1260.*
Wu et al., JACS, 2009, 131, 12915-12917.
Wu et al., JACS, 2010, 132, 13214-13216.
International Search Report and Written Opinion, application PCT/EP2012/062615, mailed Aug. 28, 2012.
Brunke et al., Rivista Italiana EPPOS, 1997, 49-82.
Cornish et al., Journal of Organomet. Chem., 1977, 132, 133-148.
Ely et al., JACS, 2010, 132, 2534-2535.
Fehr et al., Angew. Chem. Int. Ed., 2009, 48, 39, 7221-7223.
Krotz et al., Tetrahedron Asymmetry, 1990, vol. 1, n° 8, 537-540.
Shibasaki, Takahashi, J. Org. Chem., 1988, 53, 1227-1231.
Spangler et al., J. Chem. Soc. Perkin Trans. I, 1986, 1203-1207.
Spangler et al., Synthetic Commun., 1985, 15(5), 371-376.

* cited by examiner

*Primary Examiner* — Karl J Puttlitz
(74) *Attorney, Agent, or Firm* — Winston & Strawn LLP

(57) ABSTRACT

The present invention concerns a process for the preparation of a compound of formula (I) in the form of any one of its stereoisomers or mixtures thereof, wherein R represents a $C_2$-$C_{10}$ group of formula $COR^a$ wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms.

(I)

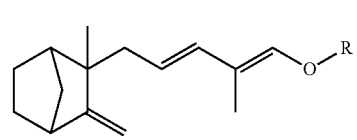

15 Claims, No Drawings

PROCESS FOR THE PREPARATION OF BETA-SANTALOL

TECHNICAL FIELD

The present invention relates to the field of organic synthesis and more specifically it concerns a process for the preparation of a compound of formula

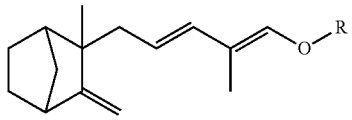
(I)

wherein R is as defined below, and said compound is in the form of any one of its stereoisomers or mixtures thereof. The invention also concerns the use of compound (I) for the synthesis of β-santalol or of derivatives thereof.

PRIOR ART

The compounds of formula (I) are useful starting materials for the preparation of β-santalol ((Z)-2-methyl-5-((1SR,2RS,4RS)-2-methyl-3-methylenebicyclo[2.2.1]heptan-2-yl)pent-2-en-1-ol, i.e. the exo isomer), and derivatives thereof, in a very short, effective and industrially feasible manner.

The β-santalol, and derivatives thereof, are well known and highly valued perfuming ingredients, some of which have particular relevance. Synthetic β-santalol is not commercially available at this time and it is only available from natural sources (Sandalwood sp. essential oils). β-santalol is present in East Indian Sandalwood Oil (*Santalum album*) at a typical level of 20-25% and is generally accepted as the principal odour vector for the fine creamy sandalwood character of the essential oil. The West Australian Sandalwood Oil (*Santalum spicatum.*) typically contains much less β-santalol, in the range of 3-8% of the essential oil, and as a result is a less appreciated oil.

The export of East Indian sandalwood and the distillation of the essential oil is under strict government control since *Santalum album* has been classified by the Convention on International Trade in Endangered Species of Wild Fauna and Flora and International Union for Conservation of Nature Red list as vulnerable and at risk of extinction.

Therefore, there is an urgent need for alternative syntheses to produce β-santalol and its dervivatives.

To the best of our knowledge, all known syntheses are lengthy or require expensive starting materials and/or reagents or even steps which are too expensive for an industrial process or generate unacceptable quantities of waste (e.g. see Brunke et al., in Rivista Italiana EPPOS, 1997, 49). In particular one may cite the following references, which are representative of the best examples of processes for the preparation of β-santalol:

EP 10213: however said process, besides the fact that it is very long, requires many chlorinated intermediates (not optimal for a use in perfumery) and provides a very low overall yield for the preparation of an enal which still require several step to be converted into the desired product;

A. Krotz et al, in *Tet. Asymm.*, 1990, 1, 537: a relatively short synthesis, however it requires expensive reducing reagents that are difficult to manipulate on large scale, expensive chiral auxiliaries and two Wittig reactions, and then subsequent transformation of a ketone into the exo-methylene group:

U.S. Pat. No. 3,662,008 and U.S. Pat. No. 3,679,756 (P&G) also describe the synthesis of β-santalol in low overall yield. This route is also dependent on a Wittig reaction to install the Z double bond and expensive reducing agents;

WO2009/141781: reports a synthesis of some derivatives of formula (I), used as intermediates in the preparation of santalol; however said synthesis is long and still passes through the same key enal intermediate as described in EP 10213;

C. Fehr et al. in *Angew. Chem., Int. Ed,* 2009, 48, 7221: describes a synthesis of β-santalol via Cu catalyzed rearrangement on an propargyl alcohol derivative which is not of easy preparation;

EP 2119714: describes a synthesis implying a Scriabine reaction on a rich aromatic ring, but nothing about the use of such reaction on an alkene or in the preparation of β-santalol;

H. Mayr et al in *Chem. Ber.,* 1986, 119, 929: describes a 1,4 electrophillic addition to a cyclic alkene but does not mention or suggest the preparation of β-santalol.

The aim of the present invention is to provide a more industrial and efficient process for the preparation of β-santalol, and derivatives thereof. Indeed, the present invention shortens the overall process of preparation of the targeted compounds by allowing the three-step preparation of santalol from santene by creating a suitably functionalised side-chain moiety (with the correct configuration) together with the concomitant formation of the methylene function (without the mandatory need of a Wittig olefination or similar transformations) using a novel reaction without literature precedent.

It is well known in the literature that despite the epi-β-santalol being present in the natural East Indian sandalwood oil, it contributes little to the overall odour impact of the oil. Thus, a selective synthesis of (Z)-β-santalol containing a minimum of epi-β-santalol, and a minimum of the (E)-β-santalol thus highly desirable.

DESCRIPTION OF THE INVENTION

A first object of the present invention is a process for the preparation of a compound of formula

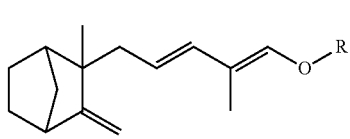
(I)

in the form of any one of its stereoisomers or mixtures thereof, wherein R represents a $C_2$-$C_{10}$ group of formula $COR^a$ wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms.

As will be shown further below, said compounds (I) are direct precursors of β-santalol (in particular (Z)-2-methyl-5-((1S,2R,4R)-2-methyl-3-methylenebicyclo[2.2.1]heptan-2-yl)pent-2-en-1-ol).

A particular aspect of the first object of the present invention is a process for the preparation of a compound of formula

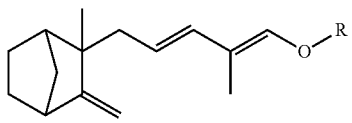
(I)

in the form of any one of its stereoisomers or mixtures thereof, and wherein R represents a $C_2$-$C_{10}$ group of formula $COR^a$ wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms;

by reacting together a compound of formula

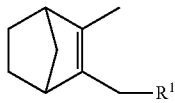
(II)

in the form of any one of its stereoisomers or mixtures thereof, and wherein $R^1$ represents a hydrogen atom or a $Si(R^2)_3$ or $B(OR^{2'})_2$ group, $R^2$ representing a $C_{1-4}$ alkyl or alkoxyl group and $R^{2'}$ representing, taken separately, a $C_{1-4}$ alkyl group or a or a phenyl group optionally substituted by one to three $C_{1-3}$ alkyl or alkoxy groups, or said $R^{2'}$, taken together, representing a $C_{2-6}$ alkanediyl group or a diphenyl or dinaphthyl group optionally substituted by one to three $C_{1-3}$ alkyl or alkoxy groups;

with a compound of formula

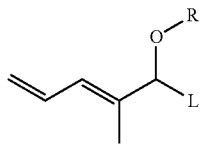
(III)

in the form of any one of its stereoisomers or mixtures thereof, and wherein R has the meaning defined in formula (I) and L represents a halogen atom or an OR group;

in the presence of 1) at least one acid selected amongst
   I. a Lewis acid selected from the group consisting of:
   i) a metal salt of a an element of the group 2, 3, 4, 13 or of a 3d element or of tin;
   ii) an alkyl aluminium chloride of formula $Al(R^4)_aCl_{3-a}$, a representing 1 or 2 and $R^4$ representing $C_{1-10}$ alkyl or alkoxide group; and
   iii) a boron derivative of formula $BZ_3$, wherein Z represents a fluoride or a phenyl group optionally substituted, and any one of its adduct with a $C_2$-$C_{10}$ ether or a $C_1$-$C_8$ carboxylic acid;
   and/or
   II. a protic acid having a $pk_a$ comprised between 2.5 and −20; and
2) optionally an additive selected amongst the group consisting of alkaline-earth hydroxide or oxide and of the compounds of formula $R^bCOCl$, $ClSi(R^b)_3$, $R^bCOOR^c$ or $(R^b\text{-}COO)_2R^d$, $R^b$ representing a $C_{1-12}$ alkyl group or a phenyl group optionally substituted by one or two $C_{1-4}$ alkyl or alkoxyl group, and $R^e$ representing a alkaline metal cation or a $R^bCO$ acyl group, and $R^d$ representing a alkaline-earth metal cation.

As well understood by a person skilled in the art, by "$pK_a$" it is understood the dissociation constant for acids which is measured at standard conditions. Said constant can be retrieved in chemical Handbooks such as "Handbook of Chemistry and Physics", 87th edition, 2006-2007, page 15-13 to 15-23, ISBN 978-0-8493-0487-3, or such as March's "Advanced Organic Chemistry" 5th edition, ISBN 0-471-58589-0, or any other similar reference.

The invention's process is, to the best of our knowledge, the first example of a Scriabine type reaction reported in the literature using an alkene instead of an aromatic compound. It is also, to the best of our knowledge, the first example of a Scriabine type reaction reported in the literature and using a diene compound of the type of formula (III).

The compound of formula (II) can be obtained according to Chem. Ber., 1955, 88, 407 (for santene, i.e. $R^1$ is a hydrogen atom).

The corresponding silyl ($R^1$=$Si(R^2)_3$) or boryl ($R^1$=B$(OR^{2'})_2$) compounds can be obtained by either 1,4 hydrosilylation, (see J. Organometallic Chem., 1977, 132, 133, J. Am. Chem. Soc., 2010, 132, 13214) or 1,4 hydroboration (see J. Am. Chem. Soc., 2009, 131, 12915, or J. Am. Chem. Soc., 2010, 132, 2534.) of the corresponding santadiene (see Chem. Ber., 1955, 88, 407). Alternatively these same products can be obtained via mono functionalisation of santene via deprotonation with Lochmann-Schlosser base as described in Chem. Ber., 1994, 127, 1401 and Chem. Ber., 1994, 127, 2135 using the appropriate reagent.

According to any embodiment of the invention, and independently of the specific aspects, said $R^1$ group represent a hydrogen atom.

Alternatively said $R^1$ group represents a $Si(R^2)_3$, $R^2$ representing a $C_{1-4}$ alkyl or alkoxyl group, or a $B(OR^{2'})_2$ group, $R^{2'}$ representing, taken separately, a $C_{1-4}$ alkyl group or a or a phenyl group optionally substituted by one to three $C_{1-3}$ alkyl or alkoxy groups, or said $R^{2'}$, taken together, representing a $C_{2-6}$ alkanediyl group or a diphenyl or dinaphthyl group optionally substituted by one to three $C_{1-3}$ alkyl or alkoxy groups.

According to any embodiment of the invention, said compound (II) is triethyl (((1SR,4RS)-3-methylbicyclo[2.2.1]hept-2-en-2-yl)methyl)silane, 2,3-dimethylbicyclo[2.2.1]hept-2-ene (santene) or 4,4,5,5-tetramethyl-2-(((1SR,4RS)-3-methylbicyclo[2.2.1]hept-2-en-2-yl)methyl)-1,3,2-dioxaborolane. In particular, said compound (II) is 2,3-dimethylbicyclo[2.2.1]hept-2-ene (santene).

The compounds of formula (III), to the best of our knowledge are novel compounds. Therefore, a second object of the invention are the novel and useful compounds of formula (III)

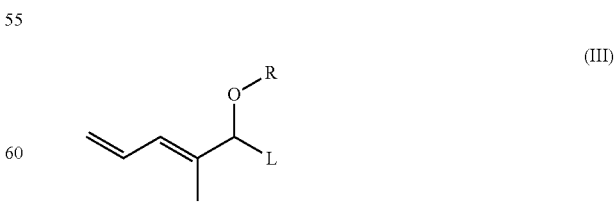
(III)

in the form of any one of its stereoisomers or mixtures thereof, and wherein R has the meaning defined in formula (I) and L represents a halogen atom or an OR group. In particular one may cite the ones wherein R is $C_{2-6}$ acyl group and L is an OR group or Cl. In particular one may cite the (E)-2-methylpenta-2,4-diene-1,1-diyl dicarboxylate, wherein by carboxylate it is meant a $C_{1-7}$, preferably a $C_{2-6}$, acyl group as defined above.

According to any embodiment of the invention, and independently of the specific aspects, said R group represents a $C_2$-$C_{10}$ group of formula $COR^a$ wherein $R^a$ is an alkyl or alkenyl group optionally comprising one or two ether functional groups or represents a phenyl or benzyl group optionally substituted by one or two $C_{1-2}$ alkyl, alkoxyl, carboxyl, acyl, amino or nitro groups or halogen atoms.

According to any embodiment of the invention, and independently of the specific aspects, said R group represents an acyl group of formula $COR^a$ wherein, and $R^a$ is
  a phenyl or benzyl group optionally substituted by one or two $C_{1-2}$ alkyl, alkoxyl, carboxyl, acyl, amino or by one or two nitro groups; or
  a linear or branched or cyclic $C_1$-$C_9$ alkyl or alkenyl group.
In particular said R group is a $C_2$-$C_7$ acyl group.

Specific examples of said R are, AcO, EtCO, $^iPrCO$, $^{sec}BuCO$, $^tBuCH_2CO$, $^tBuCO$ or $PhCH_2CO$.

According to any embodiment of the invention, and independently of the specific aspects, said L group represent a Cl atom or represents a OR group as defined above.

The process for the preparation of a compound (I), according to the invention, requires an acid, which is used as catalyst for the Scriabine type reaction.

The invention's process can be carried out in the presence of a Lewis acid of various natures, inter alia a particular metal salt. According to any embodiment of the invention, and independently of the specific aspects, said metal salt is advantageously selected amongst the compounds formula

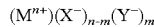

wherein
  m is an integer from 0 to (n−1), and
  n is 2 and M is Zn, Cu or an alkaline earth metal;
  n is 3 and M is a lanthanide, Sc, Fe, Al; or
  n is 4 and M is Sn, Ti or Zr;
each $X^-$ represents $Cl^-$, $Br^-$, $I^-$, a non-coordinating monoanion, $R^3SO_3^-$ wherein $R^3$ represents a chlorine or fluorine atom, or a $C_{1-3}$ hydrocarbon or perfluoro hydrocarbon, or a phenyl optionally substituted by one or two $C_{1-4}$ alkyl groups;
each $Y^-$ represents a $C_{1-6}$ carboxylate or 1,3-diketonate when n is 2 or 3, or a $C_{1-6}$ alkoxylate when n is 3 or 4.

By the expression "weakly-coordinating monoanion" it is meant the usual meaning in the art, i.e. an monoanion which is weakly-coordinated or very weakly coordinated to the metal center. Typically such weakly-coordinating monoanion are the anions of acids FIX having a $pK_a$ below 1. Non limiting examples of such non-coordinating monoanions are $ClO_4—$, $BF_4—$, $PF_6^-$, $SbCl_6^-$, $AsCl_6^-$, $SbF_6^-$, $AsF_6^-$ or $BR_4—$, wherein R is a phenyl group optionally substituted by one to five groups such as halide atoms or methyl or $CF_3$ groups, and in particular are $PF_6^-$ or $BF_4^-$.

According to any embodiment of the invention, and independently of the specific aspects, said Lewis acid is selected amongst the compounds formula

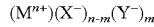

wherein
  m is an integer from 0 to (n−1), and
  n is 2 and M is Zn or Mg, Cu;
  n is 3 and M is Fe, Ce, Al; or
  n is 4 and M is Sn;
each $X^-$ represents $Cl^-$, $Br^-$, $I^-$, $PF_6^-$, $BF_4^-$, $R^3SO_3^-$ wherein $R^3$ represents a $C_{1-3}$ hydrocarbon or perfluoro hydrocarbon or a phenyl optionally substituted by one or two $C_{1-4}$ alkyl groups;
each $Y^-$ represents a $C_{1-6}$ carboxylate or 1,3-diketonate when n is 2 or 3, or a $C_{1-6}$ alkoxylate when n is 3 or 4.

According to any embodiment of the invention, said $X^-$ represents $Cl^-$, $Br^-$, $I^-$, $CF_3SO_3^-$ or $BF_4^-$ or $PF_6^-$.

According to any embodiment of the invention, when $X^-$ represents an halide, in particular $Cl^-$ or $I^-$, then $M^{n+}$ is $M^{4+}$, $Fe^{3+}$ or $Zn^{2+}$; alternatively when $X^-$ represents a non-coordinating monoanion or $R^3SO_3^-$, in particular $CF_3SO^-$ (OTf$^-$), then $M^{n+}$ is $M^{3+}$ or $M^{2+}$.

It is understood by a person skilled in the art that the nature of X may depend on the redox potential of the anions X (in particular when said anion X is an halogen) and the redox potential of the metal cation.

According to any embodiment of the invention, said $Y^-$ represents a $C_{1-6}$ carboxylate when n is 2 or 3, or a $C_{1-3}$ alkoxylate when n is 3 or 4.

According to any embodiment of the invention, and independently of the specific aspects, said metal salt is selected amongst a salt of formula
  $(Zn^{2+})(X^-)_{2-m}(Y^-)_m$, wherein m, $X^-$ and $Y^-$ have the meaning indicated above, in particular m is 0;
  $(M^{3+})(X^-)_{3-m}(Y^-)_m$, wherein m, $X^-$ and $Y^-$ have the meaning indicated above and M is Al or Fe, in particular m is 0 or 1;
  $(Sn^{4+})(Cl^-)_{4-m}(R^5O^-)_m$ wherein m has the meaning indicated above, $R^5$ representing $C_{1-3}$ alkyl group, in particular m is 0 or 1.

According to any embodiment of the invention, said metal salt is a salt of formula:
  $(Zn^{2+})(X^-)_{2-m}(Y^-)_m$, wherein m, $X^-$ and $Y^-$ have the meaning indicated above;
  $(M^{3+})(X^-)_3$, wherein m, $X^{--}$ has the meaning indicated above and M is Al or Fe;
  $(Sn^{4+})(Cl^-)_4$.

According to any embodiment of the invention, and independently of the specific aspects, said metal salt is one wherein n is 2 or 3.

The metal salt can be added to the reaction medium as a preformed salt or generated in situ, for example as described in the Examples e.g. by the reaction of a carboxylate salt (for example $Zn(AcO)_2$) with $ClSi(R^b)_3$ or $R^bCOCl$.

Said Lewis acid may be also an alkyl aluminium chloride. According to any embodiment of the invention, and independently of the specific aspects, said alkyl aluminium chloride is of formula $Al(R^4)_aCl_{3-a}$, a representing 1 or 2 and $R^4$ representing $C_{1-4}$ alkyl or alkoxide group. According to any embodiment of the invention, and independently of the specific aspects, said alkyl aluminium chloride is selected amongst the compounds of formula $Al(R^4)_aCl_{3-a}$, a representing 1 or 2 and $R^4$ representing a $C_{1-3}$ alkyl group. According to any embodiment of the invention, said alkyl aluminium chloride is a compound wherein a represents 1 and $R^4$ represents a $C_{1-3}$ alkyl group, such as $EtAlCl_2$ or $Me_2AlCl$.

Said Lewis acid may be also a boron derivative of formula $BZ_3$. According to any embodiment of the invention, and independently of the specific aspects, said boron derivative is of formula $BZ_3$, wherein Z represents a fluoride or a phenyl group optionally substituted, and any one of its adduct with a $C_2$-$C_8$ ether or a $C_1$-$C_6$ carboxylic acid. According to any embodiment of the invention, and independently of the specific aspects, said boron derivative is $BF_3$, and any one of its adduct with a $C_4$-$C_6$ ether or a $C_1$-$C_3$ carboxylic acid, such as $BF_3.(EtOEt)_{1-2}$ or $BF_3.(AcOH)_{1-2}$.

According to any embodiment of the invention, said Lewis acid is selected amongst $Me_2AlCl$, $BF_3 \cdot (HOOCMe)_{1-2}$, $(Zn^{2+})(X^-)_2$, $X^-$ being as defined above and in particular $Br^-$, $I^-$ or $Cl^-$, $FeCl_3$, $SnCl_4$, $Al(OTf)_3$.

The invention's process can be carried out in the presence of a protic acid of various natures. According to any embodiment of the invention, said protic acid is anhydrous, e.g the amount of water present in the acid is below 3% w/w.

According to any embodiment of the invention, said protic acid is selected amongst the $C_{0-12}$ sulphonic acids and the anhydrous mineral acids having a $pk_a$ comprised between 2.5 and −20.

According to any embodiment of the invention, said protic acid is selected amongst the mineral acids such as phosphomolybdinic acid, phosphoric or sulfuric acids and/or amongst the $C_{0-12}$ sulphonic acids such as $FSO_3H$, $ClSO_3H$, $MeSO_3H$, $CF_3SO_3H$, $PhSO_3H$ wherein Ph is a phenyl group optionally substituted by one or two $NO_2$, $NH_2$, $C_{1-3}$ alkyl, $C_{1-3}$ acyl $C_{1-3}$ $C_{1-3}$ carboxylic, $C_{1-3}$ alkoxyl and/or $C_{1-3}$ amino groups.

According to any embodiment of the invention, the acid used in the process is a Lewis acid.

Optionally, to said process of the invention, it can be also added, an additive. Said additive accelerate the reaction and/or provide better yield of the desired product. According to any one of the above embodiments of the invention, said additive is amongst the group consisting of the compounds of formula $R^bCOCl$, $ClSiR^b_3$, $R^bCOOR^c$ or $(R^bCOO)_2R^d$, $R^b$ representing a $C_{1-8}$, or even $C_{1-4}$, alkyl group or a phenyl group optionally substituted by one or two $C_{1-4}$ alkyl or alkoxyl group, and $R^c$ representing a Li, Na, or K cation or a $R^bCO$ acyl group, and $R^d$ representing a Mg or Ca cation.

According to any one of the above embodiments of the invention, said additive, as non limiting example, can be $ClSiMe_3$, $MeCOCl$, $AcOK$ or $AcOAc$.

In particular, when the Lewis acid is a metal salt as above defined then it is most advantageous to use an additive of the silyl or acyl chloride type. Similarly, when the Lewis acid is of the alkyl aluminium chloride type or a boron derivative as above described then it is most advantageous to use an additive of the alkali carboxylate or of the carboxylic anhydride type.

It goes without saying, as a person skilled in the art knows, that the addition of said additive, can be done in one-pot (e.g. together with the catalyst or subsequently to the catalyst, in the same reaction medium) or in a kind of a two pot process (e.g. treating compounds (II) and (III) together with the catalyst and after a purification of the product this obtained performing a treatment of said compound with the additive in a different reaction medium).

This second option (two-pot treatment) is particularly interesting in the case the Lewis acid is an alkyl aluminium chloride, since surprisingly we found that, in addition to the desired compound (I), an important product of the treatment with the Lewis acid can be a compound of formula

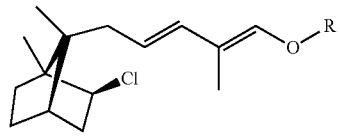

(I″)

in the form of any one of its stereoisomers or mixture thereof, and wherein R is as defined above;

and that said compound (I″) can be converted into the desired product (I), by adding an additive such as an alkali or alkaline-earth carboxylate or a carboxylic anhydride, preferably an alkali carboxylate as defined for the additive. Said compound (I″) is novel, and therefore as intermediate of compound (I) is also another aspect of the present invention.

The acid can be added to the reaction medium in a large range of concentrations. As non-limiting examples, one can cite concentrations ranging from about 0.01 to 0.30 molar equivalents, relative to the molar amount of the starting compound (III), preferably comprised between about 0.001 and 0.15 molar equivalents. As non-limiting examples, and more specifically for the protic acid, boron derivative or the metal salt, as described above, one can cite concentrations ranging from about 0.005 to 0.20 molar equivalents, relative to the molar amount of the starting compound (III), preferably comprised between about 0.007 and 0.15 molar equivalents. As non-limiting examples, and more specifically for alkyl aluminium chloride, as described above, one can cite concentrations ranging from about 0.5 to 2.00 molar equivalents, relative to the molar amount of the starting compound (III), preferably comprised between about 0.7 and 1.3 molar equivalents.

It goes without saying that the optimum concentration of the acid will depend on the nature of the latter and on the desired reaction time, as well as the presence of an additive or not.

The additive can be added to the reaction medium in a large range of concentrations. As non-limiting examples, one can cite additive concentrations ranging from 10 to 250%, relative to the weight of the acid, in particular of the Lewis acid. Preferably, the additive concentration will be comprised between 10 and 120%, relative to the weight of the acid, in particular of the Lewis acid.

The process for the preparation of a compound (I), according to the invention, can be carried out under a number of various reaction conditions, provided that they are compatible with the reagents and the reactivity of the salt and additive. A person skilled in the art is able to select the most appropriate ones in view of its own needs. According to any embodiment of the invention, and independently of the specific aspects, one may cite as non limiting examples the following conditions, independent from each other or associated in any combination:

a reaction temperature comprised between −78° C. and 150° C., preferably between 0° C. and 60° C.; of course a person skilled in the art is also able to select the preferred temperature as a function of the melting and boiling point of the starting and final products and/or an eventual solvent;

the transformation of (II) into (I), in any of its embodiments, can be carried out in absence or in the presence of solvent; non-limiting examples of such a solvent are $C_{2-10}$ saturated esters, $C_{1-6}$ saturated chlorinated solvents, $C_{6-9}$ saturated or aromatic hydrocarbon (the latter are surprising since we observed no competition in the Scriabine type reaction with the starting compound (II)) and mixtures thereof. More preferably, the solvent is 1,2-dichloroethane, dichloromethane, chlorobenzene, dichlorobenzenes, toluene or xylene.

According to any embodiment of the invention, and independently of the specific aspects, the compounds (I), (I″), or (II) can be in the form of any one of its stereoisomers or mixture thereof. For the sake of clarity by the term stereoisomer it is intended any diastereomer, enantiomer, racemate or carbon-carbon double bond isomer of configuration E or Z.

According to a particular embodiment of the invention, compound (I) is in the form of a mixture of stereoisomers comprising more than 50% (w/w) of the (1SR,2RS,4RS) stereoisomer, i.e. a compound having the relative exo configuration (the bridging carbon atom and the enol chain being in a relative cis configuration) as shown in formula (I-A)

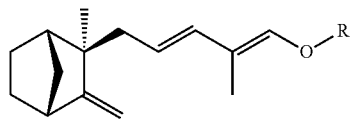

(I-A)

wherein R has the meaning indicated above in formula (I), and the bold and hatched lines indicate a relative configuration.

According to a particular embodiment of the invention, compound (I) is in the form of a mixture of stereoisomers comprising more than 50% (w/w) of the (1S,2R,4R) stereoisomer, i.e. a compound having the absolute configuration as shown in formula (I-B)

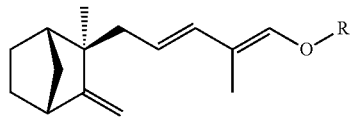

(I-B)

wherein R has the meaning indicated above in formula (I), and the bold and hatched lines indicate a absolute configuration.

It is understood that, in any of the above or below embodiments, the starting material to prepare (e.g. (II) and (I'')) or the product obtained from (e.g. see below (IV) and β-santalol) said compound (I) may have, and preferably do have, the same stereo configuration. By way of examples one may cite the following reaction scheme:

tyrate, β-santalyl propionate, comprising a step as defined above. It is understood that a person skilled in the art know how to perform said process using compound (I) obtained according to the invention's process.

The transformation of compound (I) into β-santalol can be performed in many different ways, which are well known by a person skilled in the art. Practical examples are provided in Examples herein below.

However, as non-limiting example, one of the most direct manners to transform the compound (I) into β-santalol comprises the following reactions:

a) reducing the dienol derivative (I) into a compound (IV)

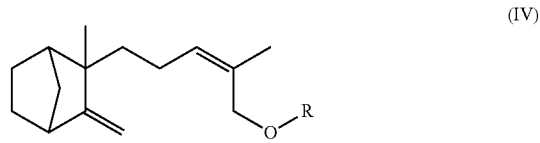

(IV)

in the form of any one of its stereoisomers or mixture thereof, and wherein R has the same meaning as in formula (I);

b) converting said compound (IV) into the β-santalol.

Steps a) and b) can be performed according to standard methods well known by a person skilled in the art.

For instance, one may cite the following method for each step:

step a): according to Shibasaki et al., in *J. Org. Chem.*, 1988, 53, 1227 (where is reported the [1,4] hydrogenation of a dienol acetate derivative) or according to WO 08/120,175 or WO 09/141,781; and step b): see WO 09/141,781.

An example of such procedure is provided in the Examples herein below.

EXAMPLES

The invention, in all its embodiments, will now be described in further detail by way of the following examples, Scheme 1:

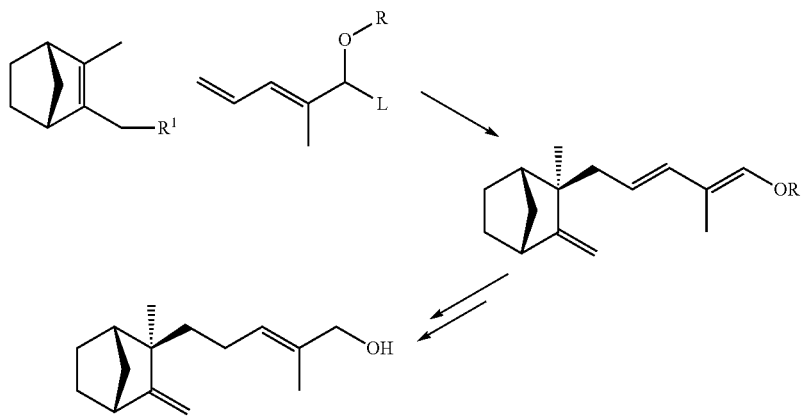

the stereo configuration being relative or absolute. So the present invention allows a three step process for β-santalol from e.g. santene.

A further object of the present invention is a process for the preparation of β-santalol, or its derivatives such as β-santalal, β-santalyl benzoate, β-santalyl butyrate, β-santalyl iso-buwherein the abbreviations have the usual meaning in the art, the temperatures are indicated in degrees centigrade (° C.); the NMR spectral data were recorded in $CDCl_3$ with a 400 MHz or 125 MHz machine for $^1H$ or $^{13}C$ respectively, the chemical shifts δ are indicated in ppm with respect to TMS as standard, the coupling constants J are expressed in Hz.

Santene: 2,3-dimethylbicyclo[2.2.1]hept-2-ene (II, R═H) was prepared according to *Chem. Ber.,* 1955, 88, 407. 2-methyl pentadienal could be prepared according to *J. Chem. Soc. Perkin Trans.* 1, 1986, 1203 or *Synth. Commun.,* 1985, 15, 371 or according to the procedure described below.

Example 1

Preparation of Compounds of Formula (III)

Preparation of (E)-ethyl 2-methylpenta-2,4-dienoate

Sodium ethoxide solution (21% in ethanol, 33.3 ml, cat.) was added to a solution of ethyl 2-methylpenta-3,4-dienoate (Bedoukian, 125.0 g, 890 mmol) in anhydrous ethanol (350 ml) and stirred at ambient temperature for 12 hours. The solution was concentrated in vacuo and the residue partitioned between ether and saturated $NH_4Cl$ solution. The aqueous phase was re-extracted twice with ether, then the combined organic phase washed with $NH_4Cl$ and then brine, dried over $Na_2SO_4$, filtered and the solvents removed in vacuo to yield the crude ester, 125.8 g as an orange oil which was used directly in the next step without further purification.

$^{13}C$ NMR: 168.4 (C), 138.2 (CH), 132.3 (CH), 128.2 (C), 124.0 ($CH_2$), 60.6 ($CH_2$), 14.3 ($CH_3$), 12.7 ($CH_3$)

Preparation of (E)-2-methylpenta-2,4-dien-1-ol $LiAlH_4$ (14.8 g, 389 mmol) was suspended in anhydrous ether (500 ml) and a solution of the ester (50.0 g, 357 mmol) in anhydrous ether (250 ml) was added slowly dropwise at such a rate as to maintain a gentle reflux. Following the addition the suspension was stirred at ambient temperature for a further 30 minutes then cooled to 0° C. in an ice bath. Distilled water (15 ml) was added extremely cautiously dropwise followed by 15% NaOH solution (15 ml) extremely cautiously followed by distilled water (45 ml). The white suspension was vigorously stirred at ambient temperature for 30 minutes then $Na_2SO_4$ was added and the suspension stirred for a further 30 minutes then filtered, the precipitate washed well with ether. The solvents were removed in vacuo to yield the crude alcohol, which was further purified by bulb to bulb distillation (0.09 mbar at 145° C.) to give the pure alcohol, 32.0 g.

$^{13}C$ NMR: 137.8 (C), 132.6 (CH), 125.4 (CH), 117.0 ($CH_2$), 68.2 ($CH_2$), 14.1 ($CH_3$)

Preparation of (E)-2-methylpenta-2,4-dienal

Manganese dioxide (45 g, 523 mmol) was added in one portion to a vigorously stirred solution of the alcohol (10.0 g, 102 mmol) in $CH_2Cl_2$ (200 ml) at ambient temperature. After 30 minutes a further portion of manganese dioxide (45 g, 523 mmol) was added in one portion followed by a further portion of 15 g. The suspension was stirred for a further 30 minutes at ambient temperature then filtered through a 6 cm plug of celite. The solid was washed with $CH_2Cl_2$. The combined washings were dried over $Na_2SO_4$ then filtered and used directly in the next step. A small portion was evaporated to dryness in vacuo (300 mbar) to yield the aldehyde.

$^{13}C$ NMR: ($CD_2Cl_2$) 195.2 (CH), 148.6 (CH), 138.4 (C), 132.0 (CH), 126.3 ($CH_2$), 9.6 ($CH_3$)

General Procedure for the Preparation of the (E)-2-methylpenta-2,4-diene-1,1-diyl-diesters The anhydride (0.306 mol) was added to a stirred solution of the freshly prepared 2-methylpentadienal (9.8 g, 0.102 mol) in $CH_2Cl_2$ (100 ml) and the solution cooled to 0° C. $FeCl_3$ anhydrous, (2% w/w, 0.15 g) was added in one portion. The solution was stirred at 0° C. for 5 hours then poured into a mixture of ether and saturated $NaHCO_3$ and stirred overnight at ambient temperature. Re-extracted twice with ether, then washed combined organic phase with saturated $NaHCO_3$ (2×), saturated $NH_4Cl$, brine, then dried over $Na_2SO_4$, filtered and the solvents removed in vacuo to yield the crude diesters. Further purification by bulb to bulb distillation gave the pure diesters.

1. Preparation of (E)-2-methylpenta-2,4-diene-1,1-diyl diacetate

Bulb to bulb distillation at 0.6 mbar at 100° C. gave the desired diacetate, 6.5 g, 32%.

$^{13}C$ NMR: 168.6 (C), 131.5 (CH), 130.9 (C), 130.7 (CH), 120.7 ($CH_2$), 92.4 (CH), 20.8 ($CH_3$), 11.3 ($CH_3$)

2. Preparation of (E)-2-methylpenta-2,4-diene-1,1-diyl propionate

Bulb to bulb distillation at 0.1 mbar at 120° C. gave the desired dipropionate, 1.8 g, 16%.

$^{13}C$ NMR: 172.2 (C), 131.5 (CH), 131.1 (C), 130.5 (CH), 120.5 ($CH_2$), 92.3 (CH), 27.4 ($CH_2$), 11.3 ($CH_3$), 8.8 ($CH_3$)

3. Preparation of (E)-2-methylpenta-2,4-diene-1,1-diyl bis(2-methylpropanoate)

Bulb to bulb distillation at 0.1 mbar at 125° C. gave the desired diisobutyrate, 6.1 g, 48%.

$^{13}C$ NMR: 174.7 (C), 131.6 (CH), 131.2 (C), 130.3 (CH), 120.4 ($CH_2$), 92.1 (CH), 34.0 (CH), 18.7, 18.6 ($CH_3$), 11.3 ($CH_3$)

Example 2

Preparation of (1E,3E)-2-methyl-5-((1SR,2RS,4RS)-2-methyl-3-methylenebicyclo[2.2.1]heptan-2-yl) penta-1,3-dien-1-yl acetate Use of $ZnBr_2$ $ZnBr_2$ (155 mg, 0.7 mmol) was added to stirred dienyl diacetate (2.5 g, 12.5 mmol) at ambient temperature. The suspension was stirred for 15 minutes at ambient temperature then a solution of santene (1.23 g, 10 mmol) in $CH_2Cl_2$ (3 ml) was added slowly dropwise. The brown suspension was stirred at ambient temperature for a further 3 hours then diluted with ethyl acetate, and $NaHCO_3$, re extracted with ethyl acetate, washed combined organic phase with $NaHCO_3$, dried over $MgSO_4$, filtered and the solvent removed in vacuo to yield the crude dienyl acetate, 3.11 g as a yellow oil.

Further purification by bulb to bulb distillation 0.12 mbar at 150-165° C., gave the desired dienyl acetate, 2.08 g. (12:1, exo:endo, yield=80%)

$^{13}C$ NMR: 167.9 (C), 165.4 (C), 134.4 (CH), 130.7 (CH), 126.8 (CH), 120.7 (C), 100.0 ($CH_2$), 46.9 (CH), 45.3 (C), 45.0 (CH), 44.5 ($CH_2$), 37.0 ($CH_2$), 29.7 ($CH_2$), 23.7 ($CH_2$), 23.0 ($CH_3$), 20.8 ($CH_3$), 10.4 ($CH_3$)

Use of $ZnCl_2$ $ZnCl_2$ (20 mg, 5 mol %) was added to the dienyl diacetate (402 mg, 2 mmol) in $CH_2Cl_2$ (2 ml) and stirred for 5 minutes at ambient temperature and then santene (240 mg, 2 mmol)

was added dropwise. The mixture was stirred at ambient temperature for a further 3 hours. Diluted with ethyl acetate then added NaHCO$_3$ stirred overnight at ambient temperature. Re-extracted with ethyl acetate, washed combined organic phase with NaHCO$_3$, filtered and the solvents removed in vacuo to yield the crude dienyl acetate, 0.48 g. Further purification by bulb to bulb at 1 mbar 165° C. gave the dienyl acetate, 0.27 g, yield=50%. (20:1, exo:endo). Spectroscopically identical to that prepared above.

Use of ZnI$_2$ and In Situ Generation of the Compound (III)

ZnI$_2$ (0.1 mmol, 3 mol %, 0.033 g) was added to a solution of dienal (0.35 g, 3.5 mmol) and santene (0.52 g, 4 mmol) in CH$_2$Cl$_2$ (3 ml) at ambient temperature. Acetic anhydride (0.5 g, 5 mmol) was added slowly dropwise over 10 minutes. Added ZnCl$_2$ (0.025 g, 1 mol %) and the solution stirred at ambient temperature for 48 hours. Then diluted with ethyl acetate then NaHCO$_3$, re-extracted with ethyl acetate, washed combined organic phase with NaHCO$_3$, dried over MgSO$_4$, filtered and the solvents removed in vacuo to yield the crude dienyl acetate, 1.0 g as a dark yellow oil.

Further purification bulb to bulb distillation 0.45 mbar at 175° C. gave the dienyl acetate, 0.46 g, yield=48% (30:1, exo:endo). Spectroscopically identical to that prepared previously.

Use of Al(OTf)$_3$

Al(OTf)$_3$ (1.7 mol %, 1.7 mmol, 811 mg) was added to toluene (25 mL) followed by santene (12.2 g, 100 mmol) at ambient temperature. Then a solution of the diene diacetate (21.8 g, 110 mmol) in toluene (25 mL) was added slowly dropwise over 45 minutes. After a further 30 minutes at ambient temperature diluted with ethyl acetate and NaHCO$_3$ solution (gas evolution), rextracted the aqueous phase with EtOAc, washed combined organic phase with NaHCO$_3$ then water, dried over MgSO$_4$, filtered and the solvents removed in vacuo to yield the crude dienyl acetate, Further purification by bulb to bulb distillation 195° C. at 8.0×10-2 mbar gave the dienyl acetate as a pale yellow oil, 17.8 g 68% exo:endo >50:1. Spectroscopically identical to that prepared previously.

Example 3

Preparation of (1E,3E)-2-methyl-5-((1SR,2RS,4RS)-2-methyl-3-methylenebicyclo[2.2.1]heptan-2-yl)penta-1,3-dien-1-yl acetate General Procedure Lewis Acid:

The Lewis acid (5-10 mol %) was added to a stirred mixture of santene (122 mg, 1 mmol) and the dienyl diacetate (180 mg, 1.1 mmol) in dichloromethane (1 ml) cooled to 0° C. After 30 minutes at 0° C. the solution was allowed to warm to ambient temperature and stirred for a further 2-4 hours at ambient temperature. Conversion analyzed by GC.

TABLE 1

Reaction catalysed by various Lewis acids

| Lewis acid (10 mol % if not specified) | % GC[1] exo | % GC[1] endo | % GC[2] Compound (I") | Ratio exo:endo |
|---|---|---|---|---|
| 0.9 eq EtAlCl$_2$ | 47 | 4 | 14 | 92:8 |
| 0.9 eq Et$_2$AlCl | 39 | 2 | 24 | 95:5 |
| 0.9 eq MeAlCl$_2$ | 38 | 3 | 5.5 | 93:7 |
| 0.9 eq Me$_2$AlCl | 53 | 3 | 12 | 95:5 |
| BF$_3$•Et$_2$O | 68 | 9 | | 88:12 |
| BF$_3$•HOAc | 74 | 10 | | 88:12 |
| Zn(OTs)$_2$ + 2 eq. TMS-Cl | 42 | 4 | 31 | 90:10 |
| Zn(acac)$_2$ + 2 eq. AcCl | 13 | 6 | 31 | 68:32 |
| Zn(acac)$_2$ + 2 eq. TMS-Cl | 56 | 11 | 12 | 84:16 |
| Zn(TFA)$_2$ + 2 eq. AcCl | 13 | 5 | 41 | 72.28 |
| Zn(TFA)$_2$ + 2 eq. TMS-Cl | 59 | 10 | 13 | 85:15 |
| Zn(oxalate) + 2 eq. AcCl | 11 | 4 | 49 | 76:24 |
| Zn(oxalate) + 2 eq. TMS-Cl | 18 | 2 | 45 | 89:11 |
| Zn(3,5-ditertBu salicylate)$_2$ + 2 eq. AcCl | 12 | 2 | 64 | 86:14 |
| Zn(3,5-ditertBu salicylate)$_2$ + 2 eq. TMS-Cl | 53 | 8 | 21 | 87:13 |
| FeCl$_3$ | 77 | 2 | | 97:3 |
| Al(BF$_4$)$_3$* | 40 | 13 | | 75/25 |
| Al(OTf)$_3$ | 72 | 1 | | 98.5:1.5 |
| Al(OPr$^i$)$_3$ + 2 eq. AcCl | 11 | 1 | | 92:8 |
| Ce(OTf)$_3$* | 53 | 1 | | 98:2 |
| Sc(OTf)$_3$* | 22 | 10 | | 75:25 |
| La(OTf)$_3$* | 26 | 0.8 | | 98:2 |
| PrOZrCl$_3$ | 18 | 0.4 | | 98:2 |
| SnCl$_4$ | 71 | 2 | | 97:3 |
| Cu(OTf)$_2$ | 30 | 15 | | 77:33 |
| Mg(OTf)$_2$ | 58 | 3 | | 94:6 |
| Cu(BF$_4$)$_2$* | 57 | 8 | | 88:12 |
| Zn(BF$_4$)$_2$ | 54 | 10 | | 5:1 |

*= 5 mol %; acac = acetylacetonate; TFA = trifluoroacetic acid; OTs = paratoluenesulfonate; OTf = trifluoromethylsulfonate
[1]= yield observed by GC of the mentioned isomer of compound (I)
[2]= yield observed by GC of the mentioned compound General Procedure Protic Acid:

Santene (61 mg, 0.5 mmol) and the dienyl diacetate (91 mg, 0.5 mmol) were dissolved in CH$_2$Cl$_2$ (1 ml) at ambient temperature. The acid catalyst was then added and the mixture stirred for the specified time at ambient temperature. The conversions are given by GC FID (%). (Based on comparison with an authentic sample.)

TABLE 2

Reaction catalysed by various protic acids

| Protic acid | Amount acid* | Time | Product** | Ratio Exo:endo |
|---|---|---|---|---|
| Phospomolybdic acid | 10 mol % | 15 mins | 63% | 50:1 |
| 2,4 dinotrobenzene sulfonic acid | 5 mol % | 15 mins | 62% | 25:1< |
| H$_2$SO$_4$ (98%) | 10 mol % | 5 mins | 49% | 50:1< |
| H3PO4 + acetic anhydride (0.5 eq) | 10 mol % | 30 mins | 43% | 20:1 |
| TriFluoroAcetic acid | 20 mol % | 12 hrs | 20% | 25:1 |
| Amberlyst 15 | 10% w/w | 12 hrs | 31% | 15:1 |
| Filtrol G13 | 10% w/w | 2 hrs | 33% | 10:1 |
| p-TolueneSulphonic acid | 10 mol % | 1 hr | 50% | 20:1< |
| HBF$_4$•(Et$_2$O)$_2$ | 5 mol % | 5 mins | 83% | 7:1 |

Mins: minutes, hrs = hours
*relative to the stating santene;
**desired product

Example 4

Preparation of (1E,3E)-2-methyl-5-((1SR,2RS,4RS)-2-methyl-3-methylenebicyclo[2.2.1]heptan-2-yl)penta-1,3-dien-1-yl carboxylate General Procedure:

Al(OTf)$_3$ (0.024 g, 1 mol %) was added in one portion to a stirred mixture of the santene (0.61 g, 5 mmol) and the 2-methylpenta-2,4-diene-1,1-diyl ester (5 mmol) at ambient temperature. After a further 60 minutes poured into saturated sodium bicarbonate and ether. Re extracted with ether, washed combined organic phase with ammonium chloride then brine, dried over sodium sulfate, filtered and the solvents removed in vacuo to yield the crude dienyl ester. Further purification by bulb to bulb distillation gave the pure dienyl ester as a mixture of exo and endo isomers.

1. (1E,3E)-2-methyl-5-((1SR,2RS,4RS)-2-methyl-3-methylenebicyclo[2.2.1]heptan-2-yl)penta-1,3-dien-1-yl propionate 5 mmol scale, bulb to bulb distillation 175° C. at 0.6 mbar gave the dienyl propionate, 0.99 g, yield=72%. (Exo:endo=50/1)

$^{13}$C NMR: 171.3 (C), 165.5 (C), 134.4 (CH), 130.7 (CH), 126.8 (CH), 120.6 (C), 100.0 (CH$_2$), 46.9 (CH), 45.3 (C), 45.0 (CH), 44.5 (CH$_2$), 37.0 (CH$_2$), 29.7 (CH$_2$), 23.7 (CH$_2$), 27.5 (CH$_3$), 23.0 (CH$_3$), 10.4 (CH$_3$), 9.0 (CH$_3$)

2. (1E,3E)-2-methyl-5-((1SR,2RS,4RS)-2-methyl-3-methylenebicyclo[2.2.1]heptan-2-yl)penta-1,3-dien-1-yl isobutyrate 5 mmol scale, bulb to bulb distillation 175° C. at 0.6 mbar gave the dienyl isobutyrate, 1.0 g, yield=70%. (Exo:endo=50/1)

$^{13}$C NMR: 173.9 (C), 165.4 (C), 134.5 (CH), 130.7 (CH), 126.8 (CH), 120.7 (C), 100.0 (CH$_2$), 46.9 (CH), 45.3 (C), 45.0 (CH), 44.5 (CH$_2$), 37.0 (CH$_2$), 29.7 (CH$_2$), 23.7 (CH$_2$), 34.0 (CH), 18.8, 18.3 (CH$_3$), 23.0 (CH$_3$), 10.4 (CH$_3$)

Example 5

Preparation of (1E,3E)-2-methyl-5-((1SR,2RS,4RS)-2-methyl-3-methylenebicyclo[2.2.1]heptan-2-yl)penta-1,3-dien-1-yl carboxylate Preparation of the Silyl Derivative of Formula (II)

Ethyldimethyl(((1SR,4RS)-3-methylbicyclo[2.2.1]hept-2-en-2-yl)methyl)silane

Triethyl aluminium (1.0 M in hexanes, 4.2 mL, 4.2 mmol) was added slowly dropwise to a suspension of Ni(acac)$_2$ (dried in vacuo 120° C. 3 hrs, 107 mg, 0.4 mmol, 5 mol %), santadiene (1.0 g, 8.3 mmol) in freshly degassed toluene (85 mL) cooled to 0° C. After 15 minutes, dimethyl ethyl silane (1.1 mL, 8.3 mmol) was added slowly dropwise and the solution was then allowed to slowly warm to ambient temperature and stirred for a further 2 hours. The reaction mixture was poured into saturated ammonium chloride solution and extracted with ether, then the combined organic phase was washed with brine and dried over Na$_2$SO$_4$, then filtered and the solvents removed in vacuo to yield the crude allyl silane 0.9 g, which was further purified by bulb to bulb distillation 30° C. at 0.08 mbar and gave the desired ally silane 0.65 g, 37%.

$^{13}$C NMR: 137.4 (C), 132.4 (C), 47.8 (CH), 47.3 (CH), 46.3 (CH$_2$), 26.2, 26.0 (CH$_2$), 15.2 (CH$_2$), 12.0 ((CH$_3$), 7.4 (CH$_3$), 7.3 (CH$_2$), −3.4 (CH$_3$) ppm.

Triethyl(((1SR,4RS)-3-methylbicyclo[2.2.1]hept-2-en-2-yl)methyl)silane

A solution of the diene (2.64 g, 22 mmol) in toluene (25 mL) containing Ni(acac)$_2$ (predried in vacuo 0.08 mbar at 120° C. for 7 hrs, 252 mg, 1 mmol) was cooled to 1° C. in an ice bath. Et$_3$Al (1.0 M in hexanes, 5.0 mL, 5 mmol) was added slowly dropwise. This solution was stirred at 0° C. for a further 15 minutes then Et$_3$SiH (2.4 g, 24 mmol) was added slowly dropwise and then the solution was stirred at ambient temperature for 2 hours. Added saturated NaHCO$_3$, and extracted the aqueous phase with ethyl acetate, washed the combined organic phase with NH$_4$Cl, brine, dried over MgSO$_4$, filtered and the solvents removed in vacuo. Further purification by bulb to bulb distillation 120-130° C. at 0.05 mbar gave desired allyl silane, 1.5 g (63%).

$^{13}$C NMR: 137.5, 132.4 (C), 47.9, 47.5 (CH), 46.3 26.4, 26.2 (CH$_2$), 12.2 (CH$_3$), 11.7 (CH$_2$), 7.5 (CH$_3$) 3.9 (CH$_2$) ppm.

Dimethoxy(methyl)(((1SR,4RS)-3-methylbicyclo[2.2.1]hept-2-en-2-yl)methyl)silane Triethyl aluminium (1.0 M in hexanes, 2.5 mL, 2.5 mmol) was added slowly dropwise to a suspension of Ni(acac)$_2$ (dried in vacuo 120° C. 3 hrs, 130 mg, 0.4 mmol, 5 mol %), santadiene (1.2 g, 10 mmol) in freshly degassed toluene (80 mL) cooled to 0° C. After 15 minutes, dimethoxy methyl silane (1.2 mL, 10 mmol) was added slowly dropwise and the solution was then allowed to slowly warm to ambient temperature and stirred for a further 2 hours. The reaction mixture was poured into saturated ammonium chloride solution and extracted with ether, then the combined organic phase was washed with brine and dried over Na2SO4, then filtered and the solvents removed in vacuo to yield the crude allyl silane 1.5 g, which was further purified by bulb to bulb distillation 75° C. at 0.08 mbar and gave the desired ally silane 1.2 g, 53%.

$^{13}$C NMR: 134.7 (C), 134.3 (C), 50.3, 50.2 (CH$_3$), 47.6 (CH), 47.4 (CH), 46.6 (CH$_2$), 26.0, 25.9 (CH$_2$), 13.5 (CH$_2$), 12.0 (CH$_3$), −5.5 (CH$_3$) ppm.

Coupling:

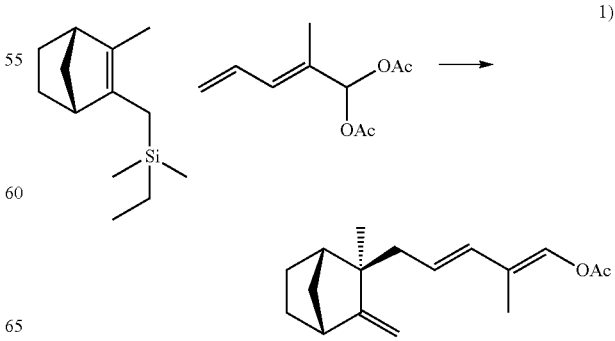

1)

Using a Lewis Acid:

ZnBr$_2$ (30 mg, 0.14 mmol) was added to a solution of the allyl silane (300 mg, 1.4 mmol), the diacetate (300 mg, 1.4 mmol) in toluene (8 mL) at ambient temperature. After 12 hours at ambient temperature GC analysis indicated 40% of the desired product plus 9% epi (endo).

Using a Protic Acid:

2,4 dinitrobenzene sulfonic acid (25 mg, 5 mol %) was added in one portion to a mixture of the dimethylethyl silyl alkene (300 mg, 1.3 mmol) and the dienyl diacetate (250 mg, 1.3 mmol) in CH$_2$Cl$_2$ (8 mL) at ambient temperature. After 15 minutes at ambient temperature GC analysis showed 63% of the desired product had formed.

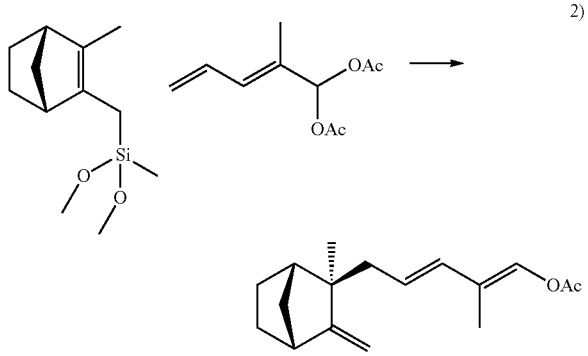
2)

Using a Lewis Acid:

ZnBr$_2$ (30 mg, 0.14 mmol 10 mol %) was added to a solution of the allyl silane (300 mg, 1.3 mmol), the diacetate (300 mg, 1.4 mmol) in CH$_2$Cl$_2$ (3 mL) at ambient temperature. After 30 minutes at ambient temperature GC analysis indicated 85% of the desired product.

Using a Protic Acid:

2,4 dinitrobenzene sulfonic acid (40 mg, 10 mol %) was added in one portion to a mixture of the dimethoxymethyl silyl alkene (300 mg, 1.3 mmol) and the dienyl diacetate (250 mg, 1.3 mmol) in CH$_2$Cl$_2$ (3 mL) at ambient temperature. After 15 minutes at ambient temperature GC analysis showed 45% of the desired product had formed.

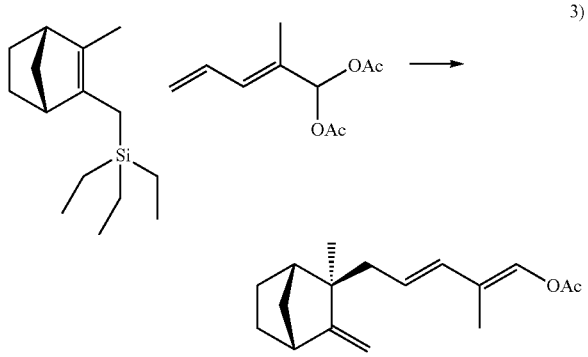
3)

Using a Lewis Acid:

ZnBr$_2$ (2.5 mol %, 7 mg) was added in one portion to a mixture of the triethylsilyl alkene (300 mg, 1.3 mmol) and the dienyl diacetate (250 mg, 1.3 mmol) in CH$_2$Cl$_2$ (3 mL) and the mixture stirred at ambient temperature then analysed by GC. 33% of the allyl silane remained and the desired product had already formed (23%).

Using a Protic Acid:

2,4 dinitrobenzene sulfonic acid (4 mg, 1 mol %) was added in one portion to a mixture of the triethyl silyl alkene (300 mg, 1.3 mmol) and the dienyl diacetate (250 mg, 1.3 mmol) in CH$_2$Cl$_2$ (3 mL) at ambient temperature. After 6 hours at ambient temperature GC analysis showed 2% of the desired product had formed.

Preparation of the Boron Derivative of Formula (II)

4,4,5,5-tetramethyl-2-(0SR,4RS)-3-methylbicyclo[2.2.1]hept-2-en-2-yl)methyl)-1,3,2-dioxoborolane Ni(COD)$_2$ (114 mg, 5 mol %), tricyclohexylphosphine (233 mg, 10 mol %) were weighed into a Schlenk flask in a glovebox, then dissolved in freshly degassed toluene (85 mL) at ambient temperature. Santadiene (freshly distilled, 1.0 g, 8.3 mmol) was added followed by pinacol borane solution (8.3 mL, 8.3 mmol, 1.0 M in THF) dropwise. The solution was stirred for 3 hours at ambient temperature then poured into saturated NaHCO$_3$ solution and extracted with ether. The organic phase was washed with water and then brine, dried over Na$_2$SO$_4$, filtered and the solvents removed in vacuo to yield the crude bononate, 1.5 g. Further purification by bulb to bulb distillation, 100° C. at 0.1 mbar gave the desired allyl boronate, 620 mg, 31%.

$^{13}$C NMR: 135.6, 134.9 (C), 83.0 (C), 47.5, 47.4 (CH), 46.6 (CH$_2$), 26.2, 25.8 (CH$_2$), 24.9, 24.8, 24.75 (CH$_3$), 11.9 (CH$_3$)

Coupling:

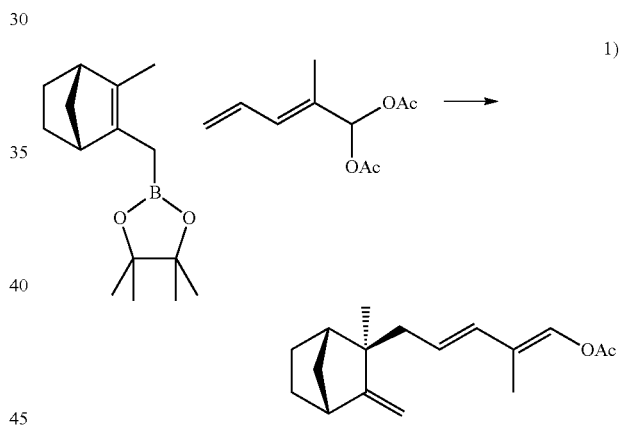
1)

ZnBr$_2$ (10 mol %, 0.05 mmol, 11 mg) was added in one portion to a stirred solution of the boronate (250 mg, 1 mmol) and the dienyl diacetate (200 mg, 1 mmol) in CH$_2$Cl$_2$ (3 mL) at ambient temperature. The suspension was stirred at ambient temperature for 6 hrs. GC analysis showed 24% boronate remained and 50% of the desired product formed.

Example 6

Preparation of (1E,3E)-2-methyl-5-((1SR,2RS,4RS)-2-methyl-3-methylenebicyclo[2.2.1]heptan-2-yl)penta-1,3-dien-1-yl acetate via compound of formula (I″)

(1E,3E)-5-((1SR,2SR,4SR,7RS)-2-chloro-1,7-dimethylbicyclo[2.2.1]hetan-7-yl)-2-methylpenta-1,3-dien-1-yl acetate (I″)

Diethyl aluminium chloride (1.0 M in hexanes, 7.2 ml, 7.2 mmol) was added dropwise over 15 minutes to a stirred solution of Santene (978 mg, 8 mmol) and the dienyl diacetate (1982 mg, 10 mmol) in $CH_2Cl_2$ (8 ml) cooled to 0° C. Stirred at 0° C. for further 90 minutes then poured into ice and saturated $NaHCO_3$, re extracted with ether, washed combined organic phase with $NaHCO_3$, dried over $Na_2SO_4$, filtered and the solvents removed in vacuo to yield the crude dienyl acetate, 1.7 g as a yellow oil.

Further purification by bulb to bulb distillation 0.12 mbar at 180° C., gave the desired dienyl acetate, 0.82 g. Identical to that prepared above. The residue contained the desired chloro dienyl acetate, 0.15 g, (yield=6%).

$^{13}$C NMR: 167.9 (C), 134.2 (CH), 130.1 (CH), 127.2 (CH), 120.7 (C), 68.2 (CH), 50.8 (C), 50.6 (C), 43.3 (CH), 42.1 ($CH_2$), 36.7 ($CH_2$), 36.4 ($CH_2$), 26.8 ($CH_2$), 20.8 ($CH_3$), 16.9 ($CH_3$), 13.5 ($CH_3$), 10.4 ($CH_3$)

(1E,3E)-2-methyl-5-((1SR,2RS,4RS)-2-methyl-3-methylenebicyclo[2.2.1]heptan-2-yl)penta-1,3-dien-1-yl acetate Treatment of the chloro dienyl acetate obtained above (150 mg) and potassium acetate (250 mg) at 150° C. gave the desired dienyl acetate spectroscopically identical to that prepared previously (yield=quantitative).

Example 7

Preparation of β-Santalol (Z)-2-methyl-5-((1SR,2RS,4RS)-2-methyl-3-methylenebicyclo[2.2.1]heptan-2-yl) pent-2-en-1-yl isobutyrate (compound of formula (IV))

The freshly distilled dienyl isobutyrate (1.0 g, 3.5 mmol) and maleic acid (25 mg, 2.2 mol %) were placed in a s/s autoclave and the catalyst $RuCp*COD.BF_4$, (30 mg, 2 mol %) was then added. Acetone (2 ml, degassed with ultrasound and argon bubbling, stored under argon) was added last and the mixture sealed, evacuated then purged with hydrogen 5 times. The suspension was stirred under an atmosphere of hydrogen 5 bars at 60° C. for 12 hours. Then filtered through a plug of silica (5 cm) with ethyl acetate as eluent then the solvents removed in vacuo to yield the crude product. Further purification by column chromatography cartridge (80 g) with 1:99 ethyl acetate:cyclohexane as eluent gave the pure isobutyrate, 0.9 g which was further purified by bulb to bulb distillation 175° C. at 0.6 mbar to give the pure desired product, 0.71 g, yield=72% as a mixture of exo:endo, 50:1, (Z:E selectivity >98:2).

$^{13}$C NMR: 177.2 (C), 166.2 (C), 131.1 (CH), 129.7 (C), 99.7 ($CH_2$), 63.0 ($CH_2$), 46.8 (CH); 44.8 (C), 44.6 (CH), 41.2 ($CH_2$), 37.1 ($CH_2$), 34.1 (CH), 29.7 ($CH_2$), 23.7 ($CH_2$), 23.4 ($CH_2$), 22.6 ($CH_3$), 21.4 ($CH_3$), 19.0 ($CH_3$)

(Z)-2-methyl-5-((1SR,2RS,4RS)-2-methyl-3-methylenebicyclo[2.2.1]heptan-2-yl)pent-2-en-1-ol (β-Santalol)

The allylic acetate (1.25 g, 4.5 mmol) was dissolved in methanol (15 ml) and sodium methoxide (23% solution in methanol, 100 µl) was added and the solution was stirred for 1 hour. The majority of the methanol was removed in vacuo then the residue was partioned between cyclohexane and water. Re-extracted with cyclohexane and then the combined organic phases washed with water, then $NaHCO_3$, dried over $K_2CO_3$ and $MgSO_4$, then filtered. The solvents were removed in vacuo to yield the crude β-santalol, 1.1 g. Further purification by bulb to bulb distillation 170° C. at 0.1 mbar gave a mixture of β-santalol and epi-β-santalol 96:4 (exo:endo), 0.9 g, yield=90% (Z:E selectivity >99:1).

$^{13}$C NMR: 166.2 (C), 133.9 (C), 129.0 (CH), 99.7 ($CH_2$), 61.6 ($CH_2$), 46.8 (CH), 44.7 (C), 44.6 (CH), 41.5 ($CH_2$), 37.1 ($CH_2$), 29.7 ($CH_2$), 23.7 ($CH_2$), 23.2 ($CH_2$), 22.6 ($CH_3$), 21.3 ($CH_3$)

What is claimed is:
1. A process for the preparation of a compound of formula

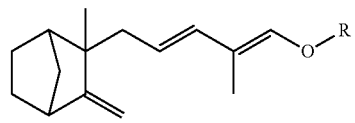

(I)

in the form of any one of its stereoisomers or mixtures thereof, and wherein R represents a $C_2$-$C_{10}$ group of formula $COR^a$ wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms;

by reacting together a compound of formula

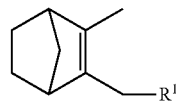

(II)

in the form of any one of its stereoisomers or mixtures thereof, and wherein $R^1$ represents a hydrogen atom or a $Si(R^2)_3$ or $B(OR^2)_2$ group, $R^2$ representing a $C_{1-4}$ alkyl or alkoxyl group and $R^{2'}$ representing, taken separately, a $C_{1-4}$ alkyl group or a or a phenyl group optionally substituted by one to three $C_{1-3}$ alkyl or alkoxy groups, or said $R^{2'}$, taken together, representing a $C_{2-6}$ alkanediyl group or a diphenyl or dinaphthyl group optionally substituted by one to three $C_{1-3}$ alkyl or alkoxy groups;

with a compound of formula

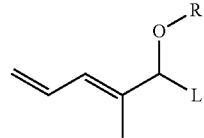

(III)

in the form of any one of its stereoisomers or mixtures thereof, and wherein R has the meaning defined in formula (I) and L represents a halogen atom or an OR group wherein R represents a $C_2$-$C_{10}$ group of formula $COR^a$ wherein $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms;

in the presence of:
1) at least one acid selected amongst
   I. a Lewis acid selected from the group consisting of:
      i) a metal salt of an element of the group 2, 3, 4, 13 or of a 3d element or of tin;

ii) an alkyl aluminium chloride of formula $Al(R^4)_aCl_{3-a}$ representing 1 or 2 and $R^4$ representing $C_{1-10}$ alkyl or alkoxide group; and iii) a boron derivative of formula $BZ_3$, wherein Z represents a fluoride or a phenyl group optionally substituted, and any one of its adduct with a $C_2$-$C_{10}$ ether or a $C_1$-$C_8$ carboxylic acid;

iv) a salt of formula $$(M^{n+})(X^-)_{n-m}(Y^-)_m$$

wherein m is an integer from 0 to (n−1), and n is 2 and M is Zn, Cu or an alkaline earth metal;

n is 3 and M is a lanthanide, Sc, Fe, Al; or n is 4 and M is Sn, Ti or Zr;

each $X^-$ represents $Cl^-$, $Br^-$, $I^-$, a non-coordinating monoanion, $R^3SO_3^-$ wherein $R^3$ represents a chlorine or fluorine atom, or a $C_{1-3}$ hydrocarbon or perfluoro hydrocarbon, or a phenyl optionally substituted by one or two $C_{1-4}$ alkyl groups;

each Y represents a $C_{1-6}$ carboxylate or 1,3-diketonate when n is 2 or 3, or a $C_{1-6}$ alkoxylate when n is 3 or 4; and/or II. a protic acid having a pka comprised between 2.5 and −20; and 2) optionally an additive selected amongst the group consisting of alkaline-earth hydroxide or oxide and of the compounds of formula $R^bCOCl$, $ClSi(R^b)_3$, $R^bCOOR^c$ or $(R^bCOO)_2R^d$, $R^b$ representing a $C_{1-10}$ alkyl group or a phenyl group optionally substituted by one or two $C_{1-4}$ alkyl or alkoxyl group, and $R^c$ representing an alkaline metal cation or a RbCO acyl group, and Rd representing an alkaline-earth metal cation.

2. A process according to claim 1, wherein $R^1$ is a hydrogen atom.

3. A process according to claim 1, wherein R is a $C_{2-7}$ acyl group.

4. A process according to claim 1, wherein the metal salt is selected amongst a salt of formula $$(M^{n+})(X^-)_{n-m}(Y^-)_m$$

wherein m is an integer from 0 to (n−1), and n is 2 and M is Zn, Cu or an alkaline earth metal;

n is 3 and M is a lanthanide, Sc, Fe, Al; or n is 4 and M is Sn, Ti or Zr;

each $X^-$ represents $Cl^-$, $Br^-$, $I^-$, a non-coordinating monoanion, $R^3SO_3^-$ wherein $R^3$ represents a chlorine or fluorine atom, or a $C_{1-3}$ hydrocarbon or perfluoro hydrocarbon, or a phenyl optionally substituted by one or two $C_{1-4}$ alkyl groups;

each Y represents a $C_{1-6}$ carboxylate or 1,3-diketonate when n is 2 or 3, or a $C_{1-6}$ alkoxylate when n is 3 or 4.

5. A process according to claim 4, wherein the metal salt is selected amongst a salt of formula $(Zn^{2+})(X^-)_{2-m}(Y^-)_m$, wherein m, $X^-$ and $Y^-$ have the meaning indicated in claim 4;

$(M^{3+})(X^-)_{3-m}(Y^-)_m$, wherein m, $X^-$ and $Y^-$ have the meaning indicated in claim 4 and M is Al or Fe;

$(Sn^{4+})(Cl^-)_{4-m}(R^5O^-)_m$ wherein m has the meaning indicated in claim 4, $R^5$ representing $C_{1-3}$ alkyl group.

6. A process according to claim 1, wherein $X^-$ represents $Cl^-$, $Br^-$, $I^-$, $CF_3SO_3^-$ or $BF_4^-$.

7. A process according to claim 1, wherein Y represents a $C_{1-6}$ carboxylate when n is 2 or 3, or a $C_{1-3}$ alkoxylate when n is 3 or 4.

8. A process according to claim 1, wherein said alkyl aluminium chloride is selected amongst the compounds of formula $Al(R^4)_aCl_{3-a}$, a representing 1 or 2 and $R^4$ representing a $C_{1-3}$ alkyl group.

9. A process according to claim 1, wherein said boron derivative is $BF_3$, and any one of its adduct with a $C_4$-$C_6$ ether or a $C_1$-$C_3$ carboxylic acid.

10. A process according to claim 1, wherein said protic acid is $C_{0-12}$ sulphonic acid or an anhydrous mineral acid.

11. A process according to claim 1, wherein said acid is a Lewis acid.

12. A process according to claim 1, wherein said additives are $ClSiMe_3$, MeCOCl, AcOK or AcOAc.

13. A process according to claim 1, wherein, in the compound of formula (III), L represents an OR group.

14. A process according to claim 1, wherein the metal salt is $ZnX_2$ wherein X represents Cl, Br, I, $CF_3SO_3$ or $BF_4$.

15. A process according to claim 1, wherein the metal salt is $Zn(CF_3SO_3)_2$.

* * * * *

UNITED STATES PATENT AND TRADEMARK OFFICE
CERTIFICATE OF CORRECTION

| | | |
|---|---|---|
| PATENT NO. | : 9,156,770 B2 | Page 1 of 1 |
| APPLICATION NO. | : 14/125876 | |
| DATED | : October 13, 2015 | |
| INVENTOR(S) | : Birkbeck | |

It is certified that error appears in the above-identified patent and that said Letters Patent is hereby corrected as shown below:

Claims

Column 20:
Line 38, Claim 1, after "a C1-4 alkyl group or a", please delete "or a".

Signed and Sealed this
Twenty-second Day of March, 2016

Michelle K. Lee
*Director of the United States Patent and Trademark Office*